United States Patent [19]

Eppstein et al.

[11] Patent Number: 5,458,140
[45] Date of Patent: Oct. 17, 1995

[54] ENHANCEMENT OF TRANSDERMAL MONITORING APPLICATIONS WITH ULTRASOUND AND CHEMICAL ENHANCERS

[75] Inventors: Jonathan A. Eppstein, Atlanta, Ga.; Deborah A. Eppstein, Salt Lake City, Utah; Joseph Kost, Omer, Israel; Robert S. Langer, Newton, Mass.

[73] Assignee: Non-Invasive Monitoring Company (NIMCO), Atlanta, Ga.

[21] Appl. No.: 152,442

[22] Filed: Nov. 15, 1993

[51] Int. Cl.$^6$ .................................................... A61B 5/00
[52] U.S. Cl. ...................... 128/632; 128/633; 128/760; 128/771
[58] Field of Search .................... 601/2; 128/632, 128/636, 637, 760, 771, 633; 604/20, 22, 289, 290

[56] References Cited

U.S. PATENT DOCUMENTS

| | | |
|---|---|---|
| 5,076,273 | 12/1991 | Schoendorfer et al. ............... 128/632 |
| 5,139,023 | 8/1992 | Stanley et al. ........................ 128/637 |
| 5,140,985 | 8/1992 | Schroeder et al. .................... 128/632 |
| 5,323,769 | 6/1994 | Bommannan ......................... 601/2 |

FOREIGN PATENT DOCUMENTS 020745  10/1993  WIPO .................................. 128/632

*Primary Examiner*—Ruth S. Smith
*Attorney, Agent, or Firm*—Thorpe, North & Western

[57] ABSTRACT

A method of enhancing the permeability of the skin or mucosa to an analyte for diagnostic purposed is described utilizing ultrasound or ultrasound plus a chemical enhancer. If desired the ultrasound may be modulated by means of frequency modulation, amplitude modulation, phase modulation and/or combinations thereof. A frequency modulation from low to high develops a local pressure gradient directed out of the body, thus permitting analytes in the body to traverse the skin and be collected and measured outside the body. The concentration of an analyte in the body is preferably determined by enhancing the permeability of the skin or other biological membrane optionally with a chemical enhancer, applying ultrasound optionally at a modulated frequency, amplitude, phase, or combinations thereof that further induces a local pressure gradient out of the body, collecting the analyte, and utilizing the analyte collection data calculating the concentration of the analyte in the body.

27 Claims, 7 Drawing Sheets

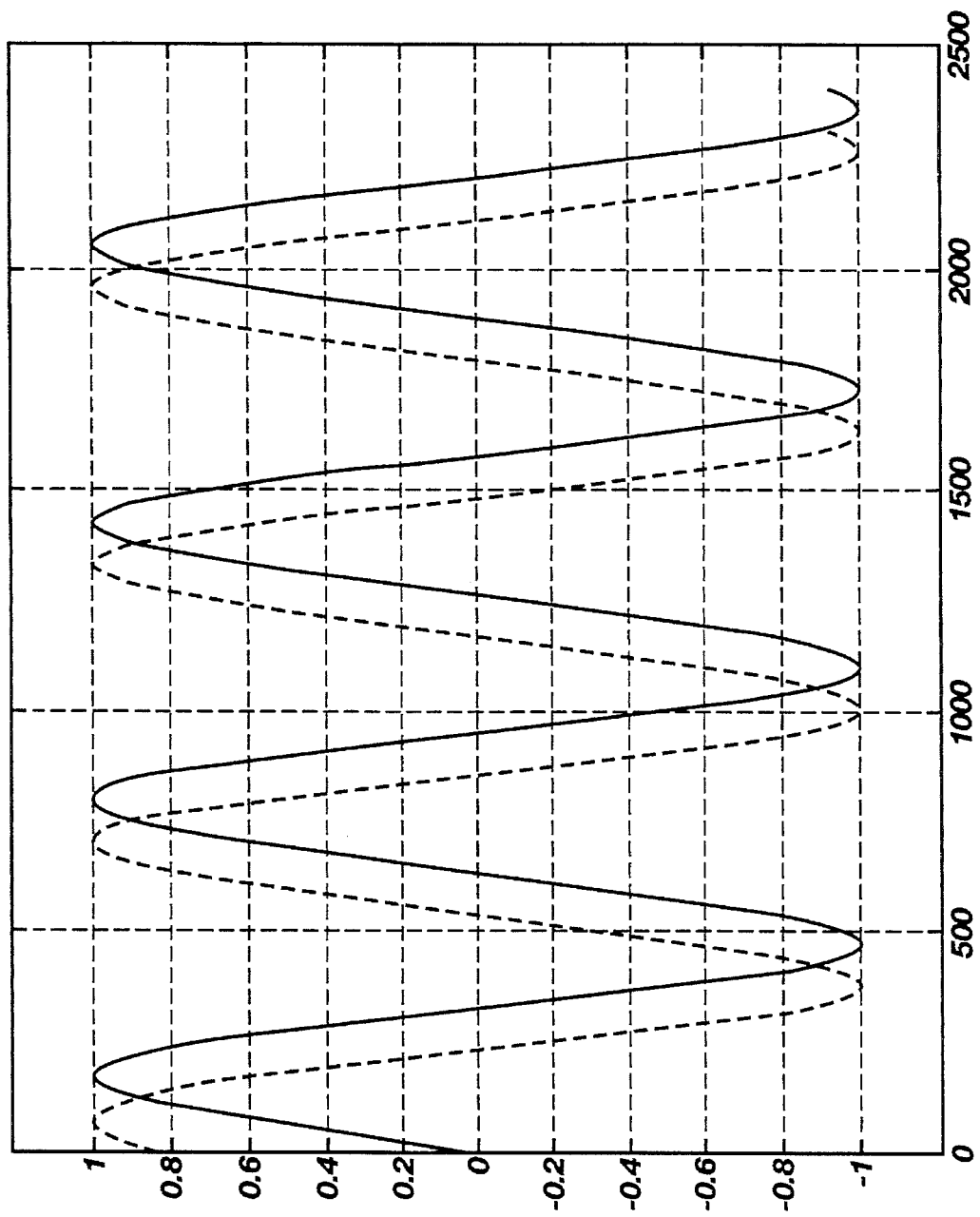

ENHANCEMENT OF TRANSDERMAL MONITORING APPLICATIONS WITH ULTRASOUND AND CHEMICAL ENHANCERS

BACKGROUND OF THE INVENTION

This invention relates generally to the field of monitoring of analytes in the body. More particularly, this invention relates to a non-invasive method of increasing the permeability of skin and other membranes through ultrasound or a combination of ultrasound and chemical enhancers for selectively enhancing outward flux of analytes from the body for monitoring thereof.

The stratum corneum is chiefly responsible for the well known barrier properties of skin. Thus, it is this layer that presents the greatest barrier to transdermal flux of drugs or other molecules into the body and of analytes out of the body. The stratum corneum, the outer horny layer of the skin, is a complex structure of compact keratinized cell remnants separated by lipid domains. Compared to the oral or gastric mucosa, the stratum corneum is much less permeable to molecules either external or internal to the body. The stratum corneum is formed from keratinocytes, which comprise the majority of epidermis cells, that lose their nuclei and become corneocytes. These dead cells then form the stratum corneum, which has a thickness of only about 10–20 μm and, as noted above, is a very resistant waterproof membrane that protects the body from invasion by exterior substances and the outward migration of fluids and dissolved molecules. The stratum corneum is continuously renewed by shedding of corneum cells during desquamation and the formation of new corneum cells by the keratinization process.

The flux of a drug or analyte across the skin can be increased by changing either the resistance (the diffusion coefficient) or the driving force (the gradient for diffusion). Flux may be enhanced by the use of so-called penetration or chemical enhancers. Chemical enhancers are well known in the art and a more detailed description will follow.

Other methods of increasing the permeability of skin to drugs have been described, such as ultrasound or iontophoresis. Iontophoresis involves the application of an external electric field and topical delivery of an ionized form of drug or an unionized drug carried with the water flux associated with ion transport (electro-osmosis). While permeation enhancement with iontophoresis has been effective, control of drug delivery and irreversible skin damage are problems associated with the technique.

Ultrasound has also been used to enhance permeability of the skin and synthetic membranes to drugs and other molecules. Ultrasound has been defined as mechanical pressure waves with frequencies above 20 kHz, H. Lutz et al., *Manual of Ultrasound* 3–12 (1984). Ultrasound is generated by vibrating a piezoelectric crystal or other electromechanical element by passing an alternating current through the material, R. Brucks et al., 6 *Pharm. Res.* 697 (1989). The use of ultrasound to increase the permeability of the skin to drug molecules has been termed sonophoresis or phonophoresis.

U.S. Pat. Nos. 4,309,989 to Fahim describes topical application of medications in a coupling agent for the treatment of Herpes virus infections and demidox mite infestations. The medications are massaged into the affected area by ultrasound to cause the medication to penetrate the skin. U.S. Pat. No. 4,372,296 to Fahim similarly describes topical application of zinc sulfate and ascorbic acid in a coupling agent for treatment of acne.

U.S. Pat. No. 4,767,402 to Kost et al. discloses a method for enhancing and controlling infusion of molecules having a low rate of permeability through skin using ultrasound in the frequency range of between 20 kHz and 10 MHz, and in the intensity range of between 0 and 3 W/cm$_2$. The molecules are either incorporated in a coupling agent or, alternatively, applied through a transdermal patch. Kost et al. further teach that the parameters of time, frequency, and power can be optimized to suit individual situations and differences in permeability of various molecules and of various skins. U.S. Pat. No. 4,780,212 to Kost et al. teaches use time, intensity, and frequency control to regulate the permeability of molecules through polymer and biological membranes. Further, the choice of solvents and media containing the molecules also affects permeation of the molecules through the membranes. Transbuccal drug delivery with ultrasound has also been disclosed, U.S. Pat. No. 4,948,587 to Kost et al. There is no suggestion however that the techniques disclosed can be utilized for the recovery of analytes.

U.S. Pat. No. 5,115,805 to Bommannan et al. discloses the use of specific frequencies (i.e. >10 MHz) of ultrasound to enhance the rate of permeation of drugs through human skin into the body. Frequencies above 10 MHz gave improved penetration of the skin above that described earlier. It is alleged that chemical penetration enhancers and/or iontophoresis can also be used in connection with the ultrasound treatment to enhance delivery of drugs through the skin into the body.

U.S. Pat. No. 5,016,615 to Driller et al. involves local application of a medication by implanting a drug-containing receptacle adjacent to a body tissue to be treated and then applying ultrasound to drive the drug out of the receptacle and into the body tissue. This method has the disadvantage of requiring surgical implantation of the drug receptacle and a noninvasive technique is preferred. U.S. Pat. No. 4,821,740 to Tachibana et al. discloses a kit for providing external medicines that includes a drug-containing layer and an ultrasonic oscillator for releasing the drugs for uptake through the surface of the skin. In U.S. Pat. No. 5,007,438 to Tachibana et al. is described an application kit in which a layer of medication and an ultrasound transducer are disposed within an enclosure. The transducer may be battery powered. Ultrasound causes the medication to move from the device to the skin and then the ultrasound energy can be varied to control the rate of administration through the skin.

Other references teaching use of ultrasound to deliver drugs through the skin include D. Bommannan et al., 9 Pharmaceutical Res. 559 (1992); D. Bommannan et al., 9 Pharmaceutical Res. 1043 (1992); K. Tachibana, 9 Pharmaceutical Res. 952 (1992); P. Tyle & P. Agrawala, 6 Pharmaceutical Res. 355 (1989); H. Benson et al., 8 Pharmaceutical Res. 1991); D. Levy et al., 83 J. Clin. Invest. 2074 (1989).

Permeation through the stratum corneum can occur by (a) intracellular penetration, (b) intercellular penetration, and (c) transappendageal penetration, especially through the sebaceous pathway of the pilosebaceous apparatus and the aqueous pathway of the salty sweat glands. The utility of ultrasound in enhancing the permeability of the stratum corneum and, consequently, increasing transdermal flux rate is thought to derive from thermal and mechanical alteration of biological tissues. The parameters of ultrasound that are manipulable to improve or control penetration include frequency, intensity, and time of exposure. All three of these parameters may be modulated simultaneously in a complex fashion to increase the effect or efficiency of the ultrasound as it relates to enhancing the transdermal molecular flux rate either into or out of the human body. Other factors also play a part, for example the composition and structure of the membrane through which molecules are to be transported, the physical and chemical characteristics of the medium in which the molecules are suspended, and the nature of the molecules themselves. Since ultrasound is rapidly attenuated in air, a coupling agent, preferably one having lowest realizable absorption coefficient that is non-staining, nonirritating, and slow drying, may be needed to efficiently transfer the ultrasonic energy from the ultrasound transducer into the skin. When a chemical enhancer fluid or anti-irritant or both are employed, they may function as the coupling agent. For example, glycerin used as an anti-irritant may also function as a coupling agent. If needed, additional components may be added to the enhancer fluid to increase the efficiency of ultrasonic transduction. In general, ultrasound exposure times for permeation through human skin have been less than 60 minutes, preferably less than 10 minutes. It has been suggested that the maximum limit of exposure should be determined by monitoring skin temperature. However, monitoring of skin surface temperature would not necessarily monitor events such as rupture of cell membranes by mechanical shear forces which could occur at low temperatures with short duration, high intensity ultrasound. The exposure may be either continuous or pulsed to reduce heating of biological membranes. Average intensities have been in the range of 0.01–5 W/cm$^2$ and are selected to be high enough to achieve the desired result and low enough to avoid significant elevation of skin temperature. Frequencies have varied from 20 kHz to 50 MHz, preferably 5–30 MHz. The depth of penetration of ultrasonic energy into living soft tissue is inversely proportional to the frequency, thus high frequencies have been suggested to improve drug penetration through the skin by concentrating the effect in the outermost skin layer, the stratum corneum. Various refractive and/or reflective ultrasonic focusing systems may also be employed to concentrate the ultrasonic energy in the desired tissue independent of the fundamental frequency. When appropriate phase conditions are met, resonance of the system can be induced to favor higher frequency harmonic components of the fundamental ultrasonic energy, causing local zones of ultrasonic energy at 2, 3, 4 or more times the fundamental frequency.

Although it has been acknowledged that enhancing permeability of the skin should theoretically make it possible to transport molecules from inside the body through the skin to outside the body for collection or monitoring, practicable methods have not been disclosed. U.S. Pat. No. 5,139,023 to Stanley et al. discloses an apparatus and method for noninvasive blood glucose monitoring. In this invention, chemical permeation enhancers are used to increase the permeability of mucosal tissue or skin to glucose. Glucose then passively diffuses through the mucosal tissue or skin and is captured in a receiving medium. The amount of glucose in the receiving medium is measured and correlated to determine the blood glucose level. However, as taught in Stanley et al., this method is much more efficient when used on mucosal tissue, such as buccal tissue, which results in detectable amounts of glucose being collected in the receiving medium after a lag time of about 10–20 minutes. However, the method taught by Stanley et al. results in an extremely long lag time, ranging from 2 to 24 hours depending on the chemical enhancer composition used, before detectable amounts of glucose can be detected diffusing through human skin (heat-separated epidermis) in vitro. These long lag times may be attributed to the length of time required for the chemical permeation enhancers to passively diffuse through the skin and to enhance the permeability of the barrier stratum corneum, as well as the length of time required for the glucose to passively diffuse out through the skin. Thus, Stanley et al. clearly does not teach a method for transporting blood glucose or other analytes non-invasively through the skin in a manner that allows for rapid monitoring as is required for blood glucose monitoring, such as with diabetic patients, and for many other body analytes, for example blood electrolytes.

In view of the foregoing problems and/or deficiencies, the development of a method for safely enhancing the permeability of the skin for noninvasive monitoring of body analytes in a more rapid time frame would be a significant advancement in the art. It would be another significant advancement in the art to provide a portable device for non-invasively enhancing the permeability of the skin to analytes inside the body, providing an energy (ultrasound) source to speed and facilitate transport of the analyte, non-invasively collecting the analyte in a collection device such as a pad, analyzing (either on an existing analyzer or on an analyzer specific for this system) and monitoring those analytes, and accurately and reproducibly calculating the concentrations of those analytes inside the body at the site and time of collection.

OBJECTS AND SUMMARY OF THE INVENTION

An object of the present invention is to provide a method for enhancing the transdermal and/or transmucosal withdrawal of analytes out from the body to be collected externally.

Another object of the invention is to controllably collect analytes from within the body through perforations in the stratum corneum, to enable the monitoring of these analytes.

Still another object of the invention is to provide a portable monitoring device for enhancing the permeability of the skin or other biological membrane so that an analyte can traverse the membrane and its concentration inside the body be determined at the site and time of collection.

These and other objects may be accomplished by applying various ultrasound frequencies to the skin, optionally with frequency, intensity and/or phase modulation, to control and enhance analyte withdrawal and collection. Near field ultrasound energy patterns are characterized by a complex distribution of local energy peaks and nulls in the x, y, and z directions. By shifting the frequency with a frequency modulation, these fine patterns also shift, causing localized, but evenly distributed movement of pressure peaks and nulls in the z axis, i.e., the direction of propagation. As the frequency is modulated from a lower frequency to a higher frequency the peak energy concentration shifts from the deeper layers of the skin toward the head of the transducer at the skin surface due to the relationship between the differing penetration range of the various frequencies and the acoustic impedance of the various tissues. Therefore, by controlling the modulation parameters, ultrasonic enhancement of transdermal/transmucosal analyte withdrawal can be selectively optimized out of the body.

Another aspect of the invention is the simultaneous use of chemical enhancers and ultrasound, optionally with modulated frequencies amplitudes and/or phases, to lower lag times of penetration of chemical enhancers through the stratum corneum and increase transdermal flux rates of selected permeants. Ultrasound energy may be used to force chemical enhancers and associated permeants into the stratum corneum, thereby reducing the lag time associated with passive diffusion. Ultrasound energy also may open up diffusional pathways in the stratum corneum, thereby increasing permeability of that layer. Ultrasound energy also can serve to enhance the flux of active permeant molecules through the skin and other biological membranes by providing an active energy source, in addition to passive diffusion, to push or pump molecules through pores and channels.

A further aspect of the invention is the use of ultrasound energy, optionally with modulations of frequency, intensity and/or phases, to controllably push and/or pump molecules through the stratum corneum via perforations introduced by needle puncture, hydraulic jet, laser, electroporation, or other methods. By modulating intensity, frequency and/or phase of the ultrasound energy, the transdermal flux rate through perforations is additionally regulated.

Still another aspect of the invention is the use of multiple ultrasound transducers to selectively direct analyte withdrawal from the body to a collection reservoir and/or absorbent patch. Transducers may be placed on either side of a fold of flesh, such as an ear lobe, or in a pattern on a single dermal or mucosal surface and be selectively energized or energized in a phased fashion or energized at separate specific frequencies, intensities and/or phases or energized with separating frequencies, amplitude and/or phase modulations to control transdermal flux in the desired direction and at the desired rate.

Yet another aspect of the invention is the use of ultrasound reflectors and/or lenses to focus or otherwise control the distribution of ultrasound energy in the skin. By judicious placement of one or more reflectors and/or lenses, directional control of transdermal flux may be achieved by manipulating ultrasound frequency and intensity parameters.

Still another aspect of the invention is a method and a portable device for achieving non-invasive transdermal collection and monitoring of analytes from the body, with analysis of analyte concentration being performed either at the site of collection or elsewhere. The method involves applying ultrasound, optionally with frequency, intensity and/or phase modulation, to rapidly deliver a chemical enhancer into the stratum corneum and thereby increase the permeability of the skin. In one aspect of practicing the invention, the parameters of the modulation are initially set to favor the delivery of the chemical enhancer into the stratum corneum and are then modified, e.g., to provide a frequency sweep from lower to higher frequencies, to provide an active pressure from inside the body to a collection and/or monitoring system on the outside of the body. Selected analytes are collected and monitored. A portable device for using this method may include couplable disposable and/or nondisposable units.

One configuration of a disposable unit comprises a system containing a reservoir for holding a chemical permeation enhancer or enhancers and a reservoir for collection of the analyte of interest. These reservoirs might be one in the same in so long as any chemical permeation enhancer or enhancers to be utilized is selected so that it will not interfere with the analysis of the analyte of interest. Alternately, the reservoir for holding the chemical permeation enhancer or enhancers can be separated from the collection reservoir, for example, by a selectively permeable membrane or with a separate additional disposable reservoir unit. The non-disposable unit can contain the ultrasound transducer, controller, and power supply. Additional electronics or optics can be included to monitor the progress of collection of the analyte. The collection reservoir, such as a filter paper or membrane, can then be removed and transported to another analyzer for analysis. Such analyzer can be a general purpose laboratory analyzer or a specialized analyzer designed to receive the specific reservoir from said device. Alternately, the analyzer device might be included in the same non-disposable unit along with the ultrasound transducer, controller, and power supply.

If the analysis is to take place at the site of collection, a number of well known techniques, [e.g. Marks et al., 1 Brit. Med. J. 293 (1965); A. Free et al., 3 Clin. Chem 163 (1957)] for measurement of analytes of clinical relevance can be used. These techniques might include, for example, chemical, immunochemical, and iontophoric techniques. Detection might be through conventional detection approaches, J. Place et. al., 1 Biosensors 321 (1985); H. Arwin et. al., 145 Analyt. Biochem. 106 (1985), or specifically designed for use with this device. The non-disposable unit can include, in the collection reservoir, chemicals or immunochemicals that react with the analyte of interest. This specific reaction might cause a change in color of the reagents, such change in color being detected using reflectance or absorbance with a light emitting diode, appropriate filter, and photodetector. This change in color can then be electronically processed and converted, through the use of standards, to indicate analyte concentration. This concentration can be displayed through a digital panel display or other suitable means to the user.

Another configuration of a disposable unit includes a reservoir for holding a chemical permeation enhancer, a source optical fiber for emitting evanescent wave energy, and a detection optical fiber positioned relative to the source fiber so as to facilitate capturing and conducting evanescent wave energy. A binder, which may be an immunochemical, for binding a specific analyte is attached to the surfaces of the optical fibers. The nondisposable unit includes an ultrasound transducer coupled to a power source. An LED source is couplable to the source optical fiber and provides light energy thereto. A photosensitive diode is couplable to the detection optical fiber and measures the evanescent wave energy received therefrom. Measurements of captured evanescent wave energy at selected times are transmitted to an integrated circuit which calculates the concentration of analyte in the individual's body and displays it on a digital panel display.

Any of the above means of analyte detection and indication of concentration can, if desired, be coupled to responsive means for delivering a drug or other permeant to the individual when the concentration of analyte monitored indicates that such delivery is warranted. For example, detection and determination of glucose concentration may be utilized to automatically activate an insulin pump or delivery of insulin from an artificial pancreas or other appropriate source. Similarly, the monitoring of other molecules and/or ions such as sodium, potassium, bilirubin, urea, ammonia, calcium, lead, iron, lithium, salicylates, and the like may be coupled to suitable delivery means when appropriate.

The time during which the ultrasound is to be applied will vary somewhat depending upon the specific means of application. Without the use of chemical enhancers the times required will be longer. When using chemical enhancers to penetrate the stratum corneum making it more susceptible to analyte withdrawal the time period can be shortened significantly. In general times of between about 1 and 30 minutes are sufficient. However, functionality is the determining factor and if any combination of ultrasound, with or without frequency and amplitude modulation, and chemical enhancers can shorten the required time for analyte collection to less than 1 minute that is also within the scope of the invention.

BRIEF DESCRIPTION OF THE DRAWINGS

FIG. 4C shows an example of phase modulation according to the present invention.

DETAILED DESCRIPTION OF THE INVENTION

Figure 1:
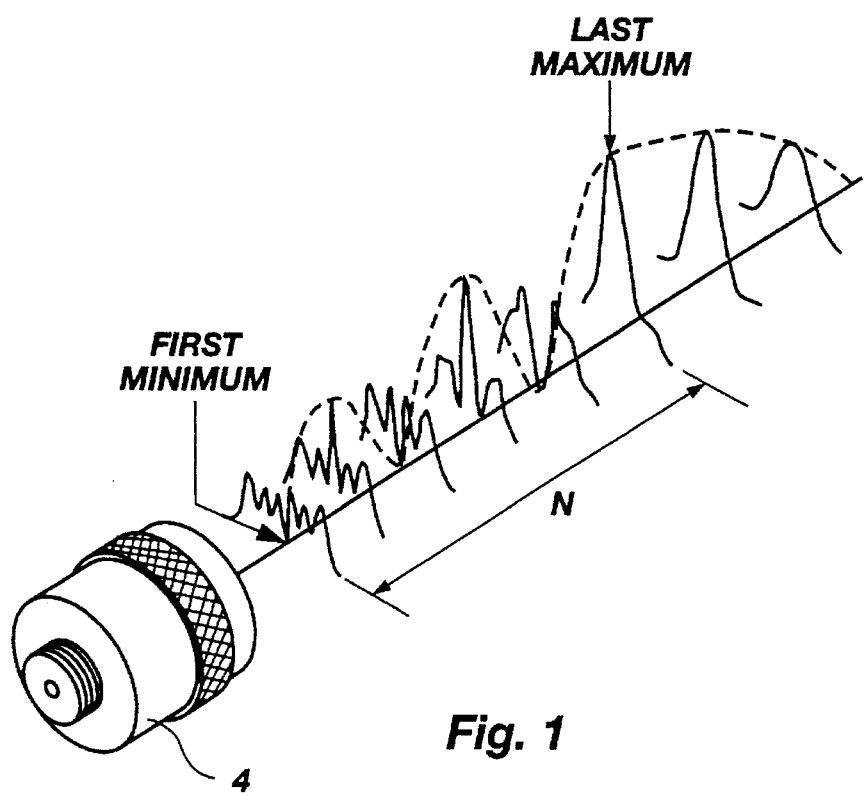
FIG. 1 shows the distribution of energy fields produced by an ultrasound transducer and division into near and far energy fields.

Although the present invention, as described herein, presents the best embodiment presently known for enhancing the transdermal flux rate of an analyte through a biological membrane and enhancing the permeability of membranes using ultrasound, it is to be understood that this invention is not limited to the particular process steps and materials disclosed herein as such process steps and materials may, of course, vary. It is also to be understood that the terminology used herein is used for the purpose of describing particular embodiments only and is not intended to be limiting since the scope of the present invention will be limited only by the appended claims.

As used herein, "penetration enhancement" or "permeation enhancement" means an increase in the permeability of skin to a drug, analyte or chemical molecule (also called "permeant"), i.e., so as to increase the rate at which a drug, analyte or chemical molecule permeates through the skin out of the body. The enhanced permeation effected through the use of such enhancers can be observed, for example, by observing diffusion of a dye, as a permeant, through animal or human skin using a diffusion apparatus.

As used herein, "chemical enhancer", "penetration enhancer" and the like shall be inclusive of all enhancers which increase the flux of a permeant, analyte or other molecule across the skin limited only by functionality. In other words, all cell envelope disordering compounds and solvents and any other chemical enhancement agents are intended to be included.

As used herein, "transdermal" or "percutaneous" means passage of a permeant into and through the skin to achieve passage of a molecule present in the body ("analyte") out through the skin so that the analyte molecule may be collected on the outside of the body.

While the invention is described herein primarily in terms of "transdermal" flux or transdermal flux rate (TFR), it will be appreciated by those skilled in the art that the present disclosed and claimed methods for increasing transdermal flux rate also encompass "transmucosal" flux using ultrasound.

"Transmucosal" is intended to mean passage of any given material through a mucosal membrane of a living organism. More specifically, "transmucosal" refers to passage from inside the organism, through a mucous membrane, into the outside environment of the organism.

As used herein, "effective" amount of a pharmacologically active agent means a sufficient amount of a compound to provide the desired local or systemic effect and performance at a reasonable benefit/risk ratio attending any medical treatment. An "effective" amount of a permeation or chemical enhancer as used herein means an amount selected so as to provide the desired increase in skin permeability.

As used herein, "carriers" or "vehicles" refer to carrier materials without significant pharmacological activity at the quantities used which are suitable for administration with other pharmaceutically active materials, and include any such materials known in the art, e.g., any liquid, gel, solvent, liquid diluent, solubilizer, or the like, that is nontoxic at the quantities employed and does not interact with the drug to be administered in a deleterious manner. Examples of suitable carriers for use herein include water, mineral oil, silicone, inorganic gels, aqueous emulsions, liquid sugars, waxes, petroleum jelly, and a variety of other oils and polymeric materials.

As used herein, a "biological membrane" is intended to mean a membrane material present within a living organism that separates one area of the organism from another and, in many instances, that separates the organism from its outer environment. Skin and mucous membranes are thus included.

As used herein, "individual" refers to both a human and an animal, to which the present invention may be applied.

As used herein, "analyte" means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, and the like.

As used herein, "transdermal flux rate" is the rate of passage of any analyte through the skin of an individual, human or animal.

As used herein, the terms "intensity amplitude", "intensity" and "amplitude" are used synonymously and refer to the amount of energy being produced by the ultrasound system.

Figure 4A:
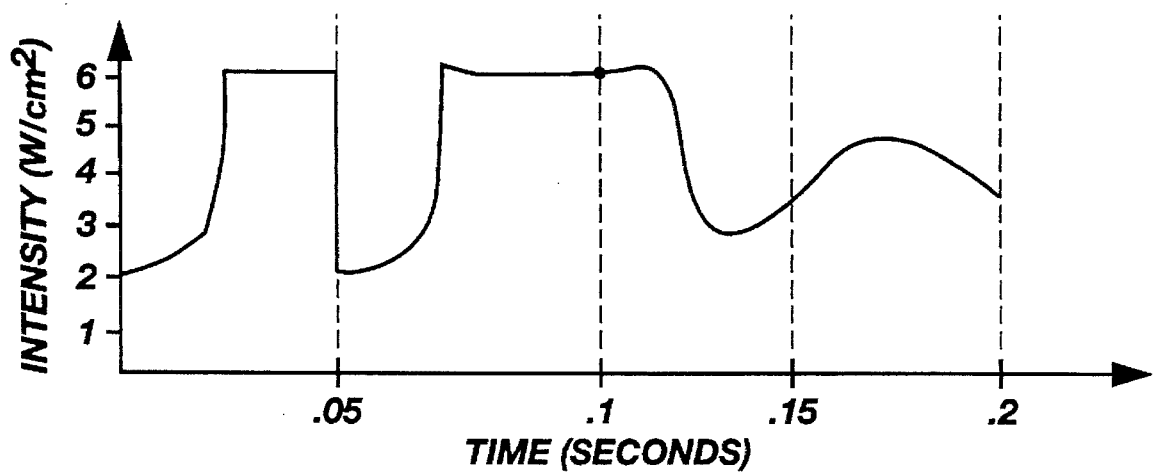
FIG. 4A shows an example of intensity modulation according to the present invention.
Figure 4B:
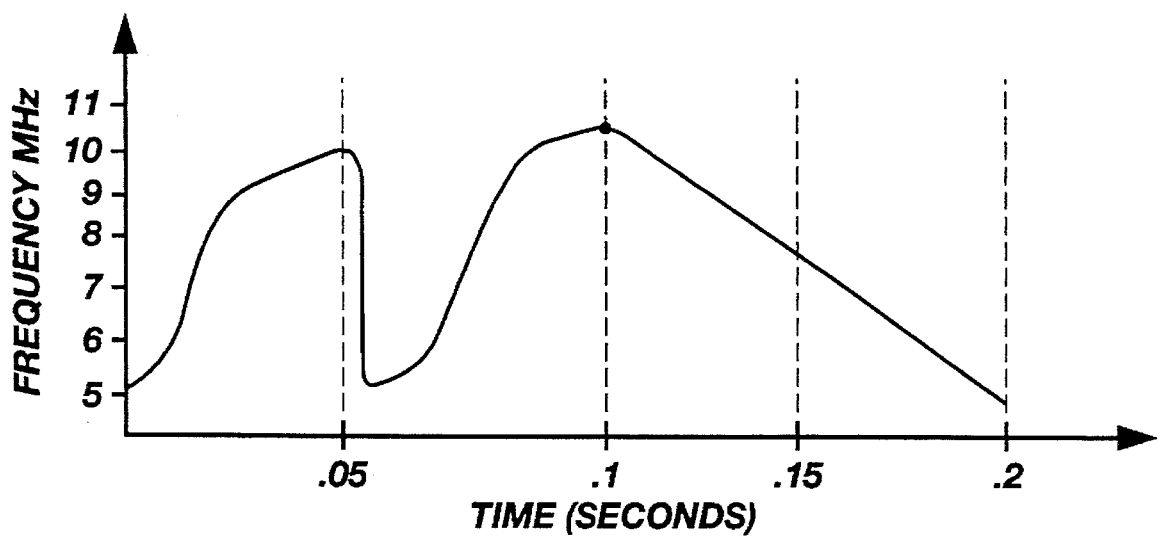
FIG. 4B shows an example of frequency modulation according to the present invention.

As used herein, "modulation" or "sweep" means a continuous, graded or stepped variation in the amplitude or frequency of ultrasound in a given time period. A frequency modulation is a graded or stepped variation in frequency in a given time period, for example 5.4–5.76 MHz in 1 sec., or 5–10 MHz in 0.1 sec., or 10–5 MHz in 0.1 sec., or any other frequency range or time period that is appropriate to a specific application. A complex modulation may include varying both the frequency and intensity simultaneously. For example, FIGS. 4A and 4B could, respectively, represent amplitude and frequency modulations being applied simultaneously to a single ultrasonic transducer.

As used herein "phase modulation" means the timing of the signal has been changed relative to its initial state shown in FIG. 4C. The frequency and amplitude of the signal may remain the same. A phase modulation can be implemented with a variable delay such as to selectively retard or advance the signal temporarily in reference to its previous state, or to another signal.

As used herein, "non-invasive" means not requiring the entry of a needle, catheter, or other invasive medical instrument into a part of the body.

The physics of ultrasound energy fields created by ultrasound transducers may be utilized in a method by which ultrasound frequency can be modulated to improve on flux rates achieved by other methods. As shown in FIG. 1, the energy distribution of an ultrasonic transducer 4 may be divided into near and far fields. The near field, characterized by length N, is the zone from the first energy minimum to the last energy maximum. The zone distal to the last maximum is the far field. The near (N) field pattern is dominated by a large number of closely spaced local pressure peaks and nulls. The length of the near field zone, N, is a function of the frequency, size and shape of the transducer face, and the speed of sound in the medium through which the ultrasound travels. For a single transducer, intensity variations within its normal operating range do not affect the nature of the sonic energy distribution other than in a linear fashion. However, for a system with multiple transducers, all being modulated in both frequency and amplitude, the relative intensities of separate transducers do affect the energy distribution in the sonic medium, regardless of whether it is skin or another medium.

By changing the frequency of the ultrasound by a modest amount, for example in the range of about 1 to 20%, the pattern of peaks and nulls remains more or less constant in a relative fashion, but the length N of the near field zone changes in direct proportion to the frequency. Changing the frequency by a large amount, say a factor of 2 or more, will most likely produce a different set of resonances or vibrational modes in the transducer, causing a significantly and unpredictably different near field energy pattern. Thus, with a modest change in the frequency of the ultrasound, the complex pattern of peaks and nulls is compressed or expanded in an accordion-like manner. By selecting the direction of frequency modulation, the direction of shift of these local pressure peaks can be controlled. By applying ultrasound at the surface of the skin, selective modulation of the ultrasound frequency controls movement of these local pressure peaks through the skin either toward the interior of the body or toward the surface of the body. A frequency modulation from high to low drives the pressure peaks into the body, whereas a frequency modulation from low to high pulls the pressure peaks from within the body toward the surface and through the skin to the outside of the body.

Assuming typical parameters for this application of, for example, a 1.27 cm diameter ultrasound transducer and a nominal operating frequency of 10 MHz and an acoustic impedance similar to that of water, a frequency modulation of 1 MHz produces a movement of about 2.5 mm of the peaks and nulls of the near field energy pattern in the vicinity of the stratum corneum. From the perspective of transdermal and/or transmucosal withdrawal of analytes, this degree of action provides access to the area well below the stratum corneum and even the epidermis, dermis, and other tissues beneath it. For any given transducer, there may be an optimal range of frequencies within which this frequency modulation is most effective.

The flux of a drug or analyte across the skin can be increased by changing either the resistance (the diffusion coefficient) or the driving force (the gradient for diffusion). Flux may be enhanced by the use of so-called penetration or chemical enhancers.

Chemical enhancers are comprised of two primary categories of components, i.e., cell-envelope disordering compounds and solvents or binary systems containing both cell-envelope disordering compounds and solvents.

Cell envelope disordering compounds are known in the art as being useful in topical pharmaceutical preparations and function also in analyte withdrawal through the skin. These compounds are thought to assist in skin penetration by disordering the lipid structure of the stratum corneum cell-envelopes. A comprehensive list of these compounds is described in European Patent Application 43,738, published Jun. 13, 1982, which is incorporated herein by reference. It is believed that any cell envelope disordering compound is useful for purposes of this invention. Exemplary of the cell envelope disordering compounds are those represented by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, —COOC$_2$H$_4$OC$_2$H$_4$OH, —COOCH(CHOH)$_4$CH$_2$OH, —COOCH$_2$CHOHCH3, —COOCH$_2$CH(OR")CH$_2$OR", —(OCH$_2$CH$_2$)$_m$OH, —COOR', or —CONR'$_2$ where R' is —H, —CH$_3$, —C$_2$H$_5$, —C$_3$H$_7$ or —C$_2$H$_4$OH; R" is —H, or a non-terminal alkenyl of about 7 to 22 carbon atoms; and m is 2–6; provided that when R" is an alkenyl and X is —OH or —COOH, at least one double bond is in the cis-configuration.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl)pyrrolidone, N-methylpyrrolidone, 1-dodecylazacycloheptan-2-one and other n-substituted-alkyl-azacycloalkyl-2-ones (azones) and the like.

U.S. Pat. No. 4,537,776, Cooper, issued Aug. 27, 1985, contains an excellent summary of prior art and background information detailing the use of certain binary systems for permeant enhancement. Because of the completeness of that disclosure, the information and terminology utilized therein are incorporated herein by reference.

Similarly, European Patent Application 43,738, referred to above, teaches using selected diols as solvents along with a broad category of cell-envelope disordering compounds for delivery of lipophilic pharmacologically-active compounds. Because of the detail in disclosing the cell-envelope disordering compounds and the diols, this disclosure of European Patent Application 43,738 is also incorporated herein by reference.

A binary system for enhancing metaclopramide penetration is disclosed in UK Patent Application GB 2,153,223 A, published Aug. 21, 1985, and consists of a monovalent alcohol ester of a C8–32 aliphatic monocarboxylic acid (unsaturated and/or branched if C18–32) or a C6–24 aliphatic monoalcohol (unsaturated and/or branched if C14–24) and an N-cyclic compound such as 2-pyrrolidone, N-methylpyrrolidone and the like.

Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

Other chemical enhancers, not necessarily associated with binary systems include DMSO or aqueous solutions of DMSO such as taught in Herschler, U.S. Pat. No. 3,551,554; Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

Some chemical enhancer systems may possess negative side effects such as toxicity, skin irritation. U.S. Pat. No. 4,855,298 discloses compositions for reducing skin irritation caused by chemical enhancer containing compositions having skin irritation properties with an amount of glycerin sufficient to provide an anti-irritating effect.

Because it is the combination of ultrasound accompanied by the use of chemical enhancers that result in the improved rate of analyte withdrawal through the stratum corneum, the specific carrier vehicle and particularly the chemical enhancer utilized may be selected from a long list of prior art vehicles some of which are mentioned above and incorporated herein by reference. To specifically detail or enumerate that which is readily available in the art is not thought necessary. The invention is not drawn to the use of chemical enhancers per se and it is believed that all chemical enhancers, useful in the delivery of drugs through the skin, will function with ultrasound in effecting measurable withdrawal of analytes from beneath and through the skin surface.

Figure 2:
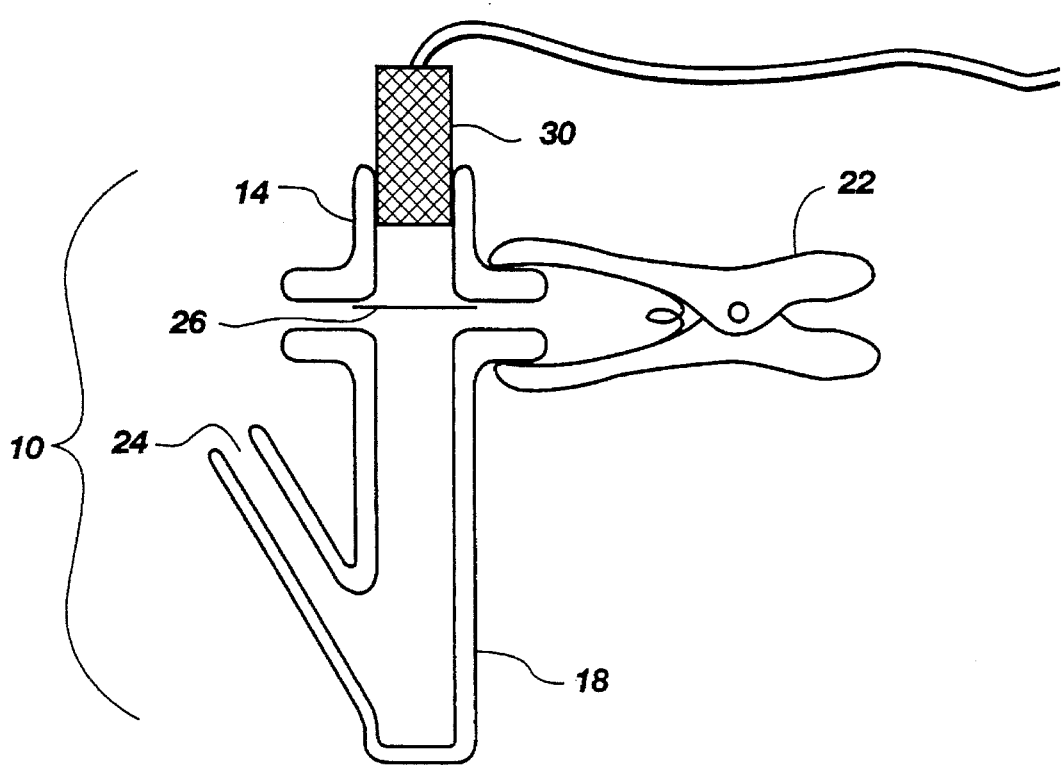
FIG. 2 shows a modified Franz cell used in testing the invention.

Modulated ultrasound and chemical enhancers were tested for their ability to control transdermal flux on human cadaver skin samples. In the tests conducted the epidermal membrane had been separated from the human cadaver whole skin by the heat-separation method of Klingman and Christopher (*Arch. Dermatol.* 88:702 (1963)) involving the exposure of the full thickness skin to 60° C. heat for 60 seconds, after which time the stratum corneum and part of the epidermis (epidermal membrane) were gently peeled off the dermis. The epidermal membrane was cut and placed between two halves of the permeation cell with the stratum corneum facing either the upper (donor) compartment or lower (receiver) compartment. Modified Franz cells were used to hold the epidermis, as shown in FIG. 2. Each Franz cell 10 consists of an upper chamber 14 and a lower chamber 18 held together with one or more clamps 22. The lower chamber 18 has a sampling port 24 through which materials may be added or removed. A sample of stratum corneum 26 is held between the upper 14 and lower 18 chambers when they are clamped together. The upper chamber 14 of each Franz cell 10 is modified to allow an ultrasound transducer 30 to be positioned within 1 cm of the stratum corneum membrane 26. Methylene blue solution was used as an indicator molecule to assess the permeation of the stratum corneum. A visual record of the process and results of each experiment was obtained in a time stamped magnetic tape format with a video camera and video cassette recorder (not shown). Additionally, samples were withdrawn for measurement with an absorption spectrometer to quantitate the amount of dye which had traversed the stratum corneum membrane during an experiment. Chemical enhancers suitable for use could vary over a wide range of solvents and/or cell envelope disordering compounds as noted above. The specific enhancer utilized was: ethanol/glycerol/water/glycerol monooleate/methyl laurate in 50/30/15/2.5/2.5 volume ratios. The system for producing and controlling the ultrasound energy included a programmable 0–30 MHz arbitrary waveform generator, a 20 watt 0–30 MHz amplifier, and two unfocused ultrasound immersion transducers having peak resonances at 15 and 25 MHz, respectively. Six cells were prepared simultaneously for testing of stratum corneum samples from the same donor. Once the stratum corneum samples were installed, they were allowed to hydrate with distilled water for at least 6 hours before any tests were done.

Effects of Ultrasound without Chemical Enhancers

As stated above, the heat-separated epidermis was placed in the Franz cells with the epidermal side facing up, and the stratum corneum side facing down, unless noted otherwise. The lower chambers were filled with distilled water, whereas the upper chambers were filled with concentrated methylene blue solution in distilled water.

EXAMPLE 1

Heat Separated Epidermis: Immediately after filling the upper chambers with methylene blue solution, ultrasound was applied to one of the cells with the transducer fully immersed. This orientation would correspond, for example, to having the transducer on the opposite side of a fold of skin, or causing the ultrasound to be reflected off a reflector plate similarly positioned and being used to 'push' analyte out of the other side of the fold into a collection device. The ultrasound setting was initially set at the nominal operating frequency of 25 MHz with an intensity equivalent to a 20 volt peak-to-peak (P-P) input wave form. This corresponds to roughly a 1 watt of average input power to the transducer and similarly, assuming the manufacturer's nominal value for conversion efficiency of 1% for this particular transducer, a sonic output power of around 0.01 watts over the 0.78 $cm^2$ surface of the active area or an ultrasonic intensity of 0.13 watts/cm$^2$. Three other control cells had no ultrasound energy applied to them. After 5 minutes the ultrasound was turned off. No visual indication of dye flux across the stratum corneum was observed during this interval in any of the cells, indicating levels less than approximately 0.0015% (v/v) of dye solution in 2 ml of receiver medium.

Testing of these same 3 control cells and 1 experimental cell was continued as follows. The intensity of ultrasound was increased to the maximum possible output available from the driving equipment of a 70 volt peak-to-peak input 12 watts average power input or ($\approx$0.13 watts/cm$^2$) of ultrasonic output intensity. Also, the frequency was set to modulate or sweep from 30 MHz to 10 MHz. This 20 MHz sweep was performed ten times per second, i.e., a sweep rate of 10 Hz. At these input power levels, it was necessary to monitor the ultrasound transducer to avoid overheating. A contact thermocouple was applied to the body of the transducer and power was cycled on and off to maintain maximum temperature of the transducer under 42° C. After about 30 minutes of cycling maximum power at about a 50% duty cycle of 1 minute on and 1 minute off, there was still no visually detectable permeation of the stratum corneum by the methylene blue dye.

A cooling water jacket was then attached to the ultrasound transducer to permit extended excitation at the maximum energy level. Using the same 3 controls and 1 experimental cell, ultrasound was applied at maximum power for 12 hours to the experimental cell. During this time the temperature of the fluid in the upper chamber rose to only 35° C., only slightly above the approximately 31° C. normal temperature of the stratum corneum in vivo. No visual evidence of dye flux through the stratum corneum was apparent in any of the four cells after 12 hrs. of ultrasound applied as described above.

EXAMPLE 2

Perforated Stratum Corneum: Six cells were prepared as described above. The clamps holding the upper and lower chambers of the Franz cells were tightened greater than the extent required to normally seal the upper compartment from the lower compartment, and to the extent to artificially introduce perforations and "pinholes" into the heat-separated epidermal samples. When dye solution was added to the upper chamber of each cell, there were immediate visual indications of leakage of dye into the lower chambers through the perforations formed in the stratum corneum. Upon application of ultrasound to cells in which the stratum corneum was so perforated with small "pinholes," a rapid increase in the transport of fluid through a pinhole in the stratum corneum was observed. The rate of transport of the indicator dye molecules was directly related to whether the ultrasound was applied or not. That is, application of the ultrasound caused an immediate (lag time approximately <0.1 second) pulse of the indicator molecules through the pinholes in the stratum corneum. This pulse of indicator molecules ceased immediately upon turning off of the ultrasound (a shutoff lag of approximately <0.1 second). The pulse could be repeated as described.

Effects of Ultrasound and Chemical Enhancers

Two different chemical enhancer formulations were used. Chemical Enhancer One or CE1 was an admixture of ethanol/glycerol/water/glycerol monooleate/methyl laurate in a 50/30/15/2.5/2.5 volume ratio. These are components generally regarded as safe, i.e. GRAS, by the FDA for use as pharmaceutical excipients. Chemical Enhancer Two or CE2 is an experimental formulation shown to be very effective in enhancing transdermal drug delivery, but generally considered too irritating for long term transdermal delivery applications. CE2 contained ethanol/glycerol/water/lauradone/methyl laurate in the volume ratios 50/30/15/2.5/2.5. Lauradone is the lauryl (dodecyl) ester of 2-pyrrolidone-5-carboxylic acid ("PCA") and is also referred to as lauryl PCA.

EXAMPLE 3

Six Franz cells were set up as before except that the heat separated epidermis was installed with the epidermal layer down, i.e., stratum corneum side facing up. Hydration was established by exposing each sample to distilled water overnight. To begin the experiment, the distilled water in the lower chambers was replaced with methylene blue dye solution in all six cells. The upper chambers were filled with distilled water and the cells were observed for about 30 minutes confirming no passage of dye to ensure that no pinhole perforations were present in any of the cells. When none were found, the distilled water in the upper chambers was removed from four of the cells. The other two cells served as distilled water controls. The upper chambers of two of the experimental cells were then filled with CE1 and the other two experimental cells were filled with CE2.

Ultrasound was immediately applied to one of the two CE2 cells. A 25 MHz transducer was used with the frequency sweeping every 0.1 second from 10 MHz to 30 MHz at maximum intensity of $\approx$0.13 watts/cm$^2$. After 10–15 minutes of ultrasound applied at a 50% duty cycle, dye flux was visually detected. No dye flux was detected in the other five cells.

Ultrasound was then applied to one of the two cells containing CE1 at the same settings. Dye began to appear in the upper chamber within 5 minutes. Thus, ultrasound together with a chemical enhancer significantly increased the transdermal flux rate of a marker dye through the stratum corneum, as well as reduced the lag time.

EXAMPLE 4

Formulations of the two chemical enhancers were prepared minus the glycerin and these new formulations, designated CE1MG and CE2MG, were tested as before. Water was substituted for glycerin so that the proportions of the other components remained unchanged. Three cells were prepared in modified Franz cells with the epidermal side of the heat separated epidermis samples facing toward the upper side of the chambers. These samples were then hydrated in distilled water for 8 hours. After the hydration step, the distilled water in the lower chambers was replaced with either CE1MG or CE2MG and the upper chamber was filled with the dye solution. Ultrasound was applied to each of the three cells sequentially.

Upon application of pulsed, frequency-modulated ultrasound for a total duration of less than 10 minutes, a significant increase in permeability of the stratum corneum samples was observed. The permeability of the stratum corneum was altered relatively uniformly across the area exposed to both the chemical enhancer and ultrasound. No "pinhole" perforations through which the dye could traverse the stratum corneum were observed. The transdermal flux rate was instantly controllable by turning the ultrasound on or off. Turning the ultrasound off appeared to instantly reduce the transdermal flux rate such that no dye was visibly being actively transported through the skin sample; presumably the rate was reduced to that of passive diffusion. Turning the ultrasound on again instantly resumed the high level flux rate. The modulated mode appeared to provide a regular pulsatile increase in the transdermal flux rate at the modulated rate. When the ultrasound was set to a constant frequency, the maximum increase in transdermal flux rate for this configuration seemed to occur at around 27 MHz.

Having obtained the same results with all three samples, the cells were then drained of all fluids and flushed with distilled water on both sides of the stratum corneum. The lower chambers were then immediately filled with distilled water and the upper chambers were refilled with dye solution. The cells were observed for 30 minutes. No holes in the stratum corneum samples were observed and no large amount of dye was detected in the lower chambers. A small amount of dye became visible in the lower chambers, probably due to the dye and enhancer trapped in the skin samples from their previous exposures. After an additional 12 hours, the amount of dye detected was still very small.

EXAMPLE 5

Perforated Stratum Corneum: Three cells were prepared with heat-separated epidermis samples with the epidermal side facing toward the upper side of the chamber from the same donor as in Example 4. The samples were hydrated for 8 hours and then the distilled water in the lower chambers was replaced with either CE1MG or CE2MG. The upper chambers were then filled with dye solution. Pinhole perforations in the stratum corneum samples permitted dye to leak through the stratum corneum samples into the underlying enhancer containing chambers. Ultrasound was applied. Immediately upon application of the ultrasound, the dye molecules were rapidly pushed through the pores. As in example 2, the rapid flux of the dye through the pores was directly and immediately correlated with the application of the ultrasound.

EXAMPLE 6

A low cost ultrasound transducer, TDK #NB-58S-01 (TDK Corp.), was tested for its capability to enhance transdermal flux rates. The peak response of this transducer was determined to be about 5.4 MHz with other local peaks occurring at about 7 MHz, 9 MHz, 12.4 MHz, and 16 MHz.

This TDK transducer was then tested at 5.4 MHz for its ability to enhance transdermal flux rate in conjunction with CE1MG. Three cells were set up with the epidermal side facing the lower chamber, then the skin samples were hydrated for 8 hrs. The dye solution was placed in the lower chamber. The transducer was placed in the upper chamber immersed in CE1MG. Using swept frequencies from 5.3 to 5.6 MHz as the ultrasound excitation, significant quantities of dye moved through the stratum corneum and were detected in the collection well of the cell in 5 minutes. Local heating occurred, with the transducer reaching a temperature of 48° C. In a control using CE1MG without ultrasound, a 24 hour exposure yielded less dye in the collection well than the 5 minute exposure with ultrasound.

This example demonstrates that a low cost, low frequency ultrasound transducer can strikingly affect transdermal flux rate when used in conjunction with an appropriate chemical enhancer. Although higher frequency ultrasound will theoretically concentrate more energy in the stratum corneum, when used with a chemical enhancer, the lower frequency modulated ultrasound can accelerate the transdermal flux rate to make the technology useful and practical.

EXAMPLE 7

Figure 3A:
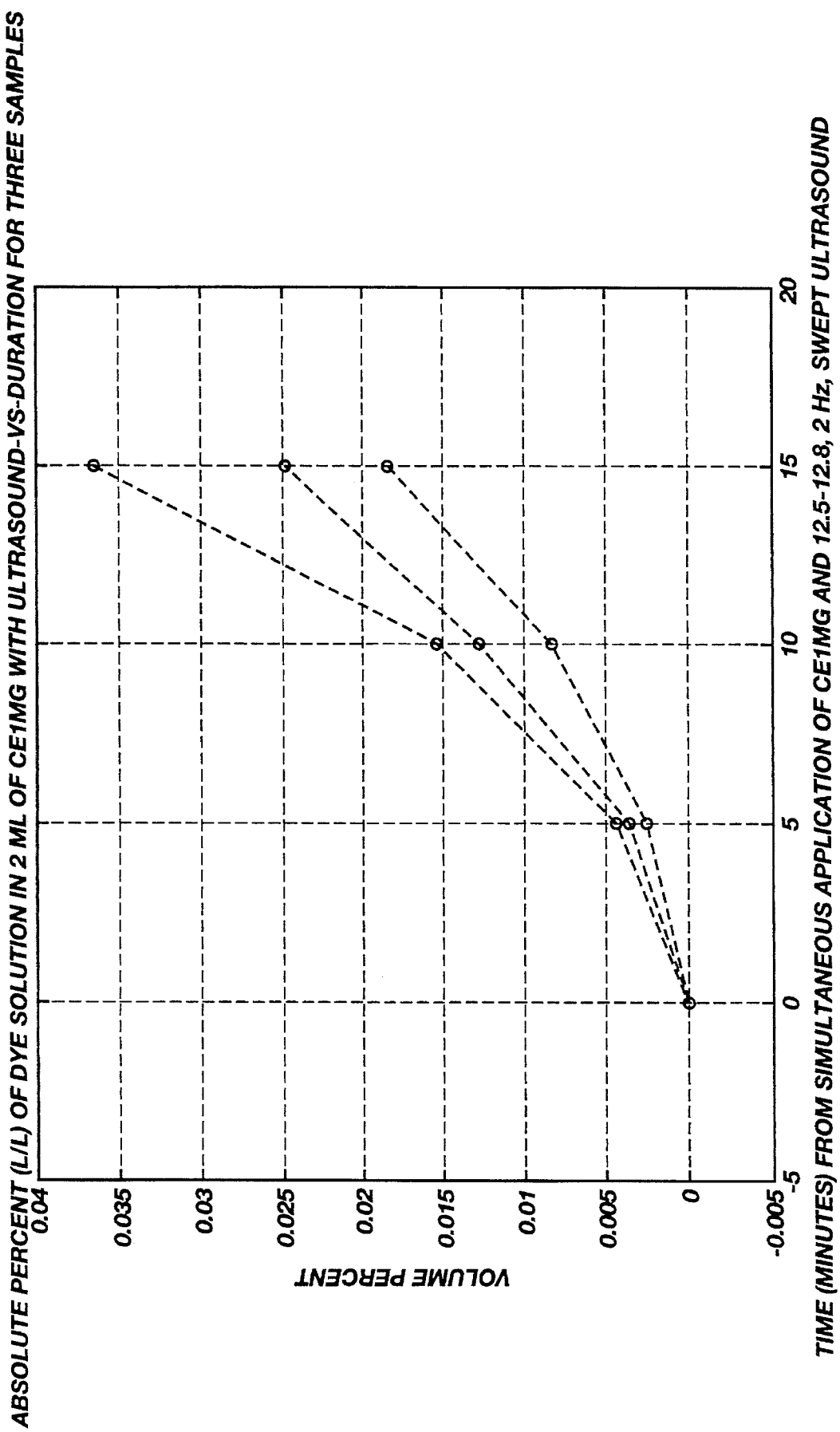
FIG. 3A shows one embodiment of dye flux across human skin obtained using ultrasound in conjunction with a chemical enhancer.
Figure 3B:
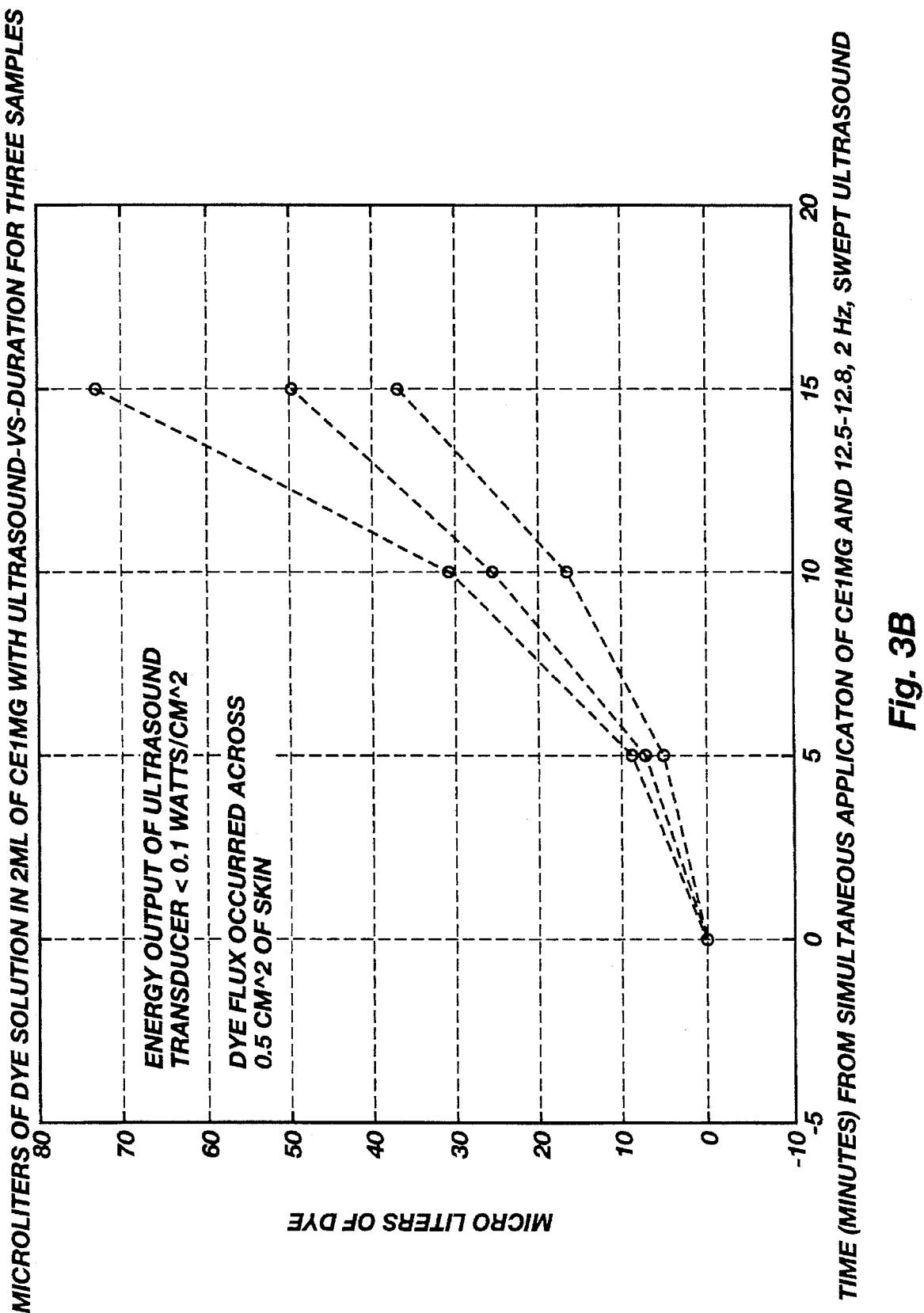
FIG. 3B shows another embodiment of dye flux across human skin obtained using ultrasound in conjunction with a chemical enhancer.

Demonstration of molecule migration across human skin: Tests with the TDK transducer and CE1MG described in Example 6 were repeated at about 12.4 MHz, one of the highest local resonant peaks for the transducer, with a frequency sweep at a 2 Hz rate from 12.5 to 12.8 MHz and an ultrasonic energy density less than 0.1 W/cm$^2$. The epidermal side of the heat-separated epidermis was facing down, the dye solution was in the lower chamber, and the enhancer solution and the ultrasound were placed in the upper chamber. The results of this experiment are shown in FIGS. 3A and 3B. Within 5 minutes a significant amount of dye had moved across the stratum corneum into the collection well. Ohmic heating in the transducer was significantly less than with the same transducer being driven at 5.4 MHz, causing an increase in temperature of the chemical enhancer to only about 33° C.

Even at these low efficiency levels, the results obtained with CE1MG and ultrasound from the TDK transducer were remarkable in the monitoring direction. FIGS. 3A and 3B show plots of data obtained from three separate cells with the TFR measured in the monitoring direction. Even at the 5 minute time point, readily measurable quantities of the dye were present in the chemical enhancer on the outside of the stratum corneum, indicating transport from the epidermal side through the stratum corneum to the "outside" area of the skin sample.

To optimize the use of the ultrasound or the ultrasound/chemical enhancer approach for collecting and monitoring analytes from the body, means for assaying the amount of analyte of interest are required. An assay system that takes multiple readings while the unit is in the process of withdrawing analytes by ultrasound with or without chemical enhancers makes it unnecessary to standardize across a broad population base and normalize for different skin characteristics and flux rates. By plotting two or more data points in time as the analyte concentration in the collection system is increasing, a curve-fitting algorithm may be applied to determine the parameters describing the curve relating analyte withdrawal or flux rate to the point at which equilibrium is reached, thereby establishing the measure of the interval concentration. The general form of this curve is invariant from one individual to another; only the parameters change. Once these parameters are established, solving for the steady state solution (i.e., time equals infinity) of this function, i.e., when full equilibrium is established, provides the concentration of the analyte within the body. Thus, this approach permits measurements to be made to the desired level of accuracy in the same amount of time for all members of a population regardless of individual variations in skin permeability.

Several existing detection techniques currently exist that are adaptable for this application. See, D. A. Christensen, in 1648 Proceedings of Fiber Optic, Medical and Fluorescent Sensors and Applications 223–26 (1992). One method involves the use of a pair of optical fibers that are positioned close together in an approximately parallel manner. One of the fibers is a source fiber, through which light energy is conducted. The other fiber is a detection fiber connected to a photosensitive diode. When light is conducted through the source fiber, a portion of the light energy, the evanescent wave, is present at the surface of the fiber and a portion of this light energy is collected by the detection fiber. The detection fiber conducts the captured evanescent wave energy to the photosensitive diode which measures it. The fibers are treated with a binder to attract and bind the analyte that is to be measured. As analyte molecules bind to the surface (such as the analyte glucose binding to immobilized lectins such as concanavalin A, or to immobilized anti-glucose antibodies) the amount of evanescent wave coupling between the two fibers is changed and the amount of energy captured by the detection fiber and measured by the diode is changed as well. Several measurements of detected evanescent wave energy over short periods of time support a rapid determination of the parameters describing the equilibrium curve, thus making possible calculation of the concentration of the analyte within the body. The experimental results showing measurable flux within 5 minutes (FIGS. 3A and 3B) with this system suggest sufficient data for an accurate final reading are collected within 5 minutes.

In its most basic embodiment, a device that can be utilized for the application of ultrasound and collection of analyte comprises an absorbent pad, either of natural or synthetic material, which serves as a reservoir for the chemical enhancer, if used, and for receiving the analyte from the skin surface. The pad or reservoir is held in place, either passively or aided by appropriate fastening means, such as a strap or adhesive tape, on the selected area of skin surface.

An ultrasonic transducer is positioned such that the pad or reservoir is between the skin surface and the transducer, and held in place by appropriate means. A power supply is coupled to the transducer and activated by switch means or any other suitable mechanism. The transducer is activated to deliver ultrasound, modulated in frequency, phase or intensity, as desired, to deliver the chemical enhancer, if used, from the reservoir through the skin surface followed by collection of the analyte from the skin surface into the reservoir. After the desired fixed or variable time period, the transducer is deactivated. The pad or reservoir, now containing the analyte of interest, can be removed to quantitate the analyte, for example, by a laboratory utilizing any number of conventional chemical analyses, or by a portable device. Alternately, the mechanism for quantitating the analyte can be build into the device used for collection of the analyte, either as an integral portion of the device or as an attachment.

EXAMPLE 8

Figure 5:
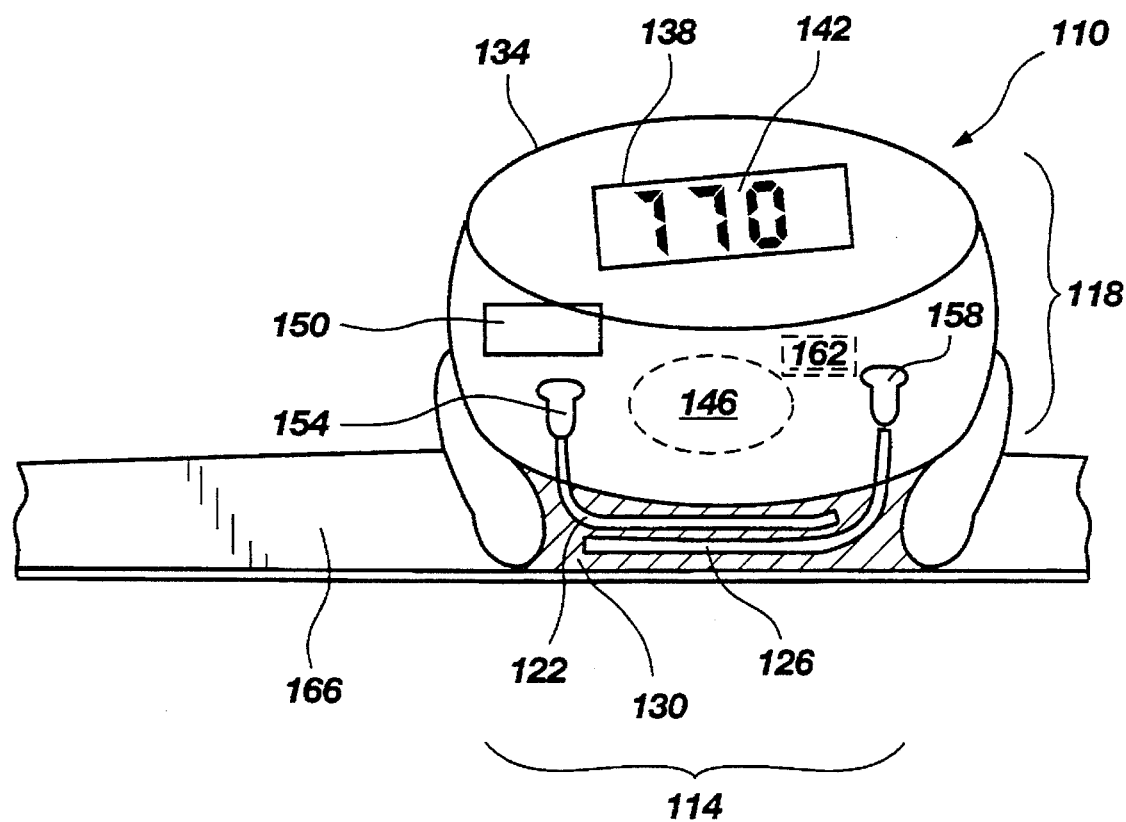
FIG. 5 shows an example of a portable device for enhancing the transdermal flux rate of the skin, collecting an analyte from the body of an individual, and calculating the concentration of the analyte in the body of the individual.

FIG. 5 shows an embodiment of a portable monitoring device for using this method of collecting and monitoring analytes with the aid of ultrasound and chemical enhancer. The monitoring device 110 contains disposable 114 and non-disposable 118 units which are couplable together. The disposable unit 114 contains a source fiber 122, a detection fiber 126, and a reservoir 130 for holding a chemical enhancer. Both the source fiber 122 and the detection fiber 126 are optical fibers capable of transmitting light energy and have exposed on their exterior surfaces a binder capable of binding an analyte. The binder is selected according to the analyte that is to be monitored. The reservoir may be an absorbent paper or pad saturated with the enhancer formulation, or a liquid reservoir (e.g., a TheraDerm-LRS™ patch manufactured by TheraTech, Inc., Salt Lake City, Utah), or other suitable unit for containing the enhancer formulation. The non-disposable unit 118 contains a cover 134 for protecting the internal components of the non-disposable unit 118. Built into the cover 134 is an opening 138 through which an LCD display 142 is visible. In the interior of the non-disposable unit 118 is an ultrasonic transducer 146 which is connected to a power source, such as a battery 150. The transducer 146 is positioned to be over the reservoir 130 so that, when the monitoring device 110 is placed on the skin 166 of an individual, the reservoir lies between the skin 166 and the transducer 146. Also in the interior of the non-disposable unit 118 are a light source 154, which may be an LED, laser diode, or other source of optical energy, and detector 158 capable of converting the incoming optical energy into an electrical signal. The detector 158 may be a photo diode, a photo multiplier tube, and the like. An integrated circuit 162 is coupled to the transducer 146, the light source 154, the photosensitive diode 158, the output device 142, and the battery 150. When the disposable unit 114 and the non-disposable unit 118 are coupled together, the source fiber 122 is coupled to the light source 154 so that light energy may be produced by the light source 154 and transmitted through the source fiber 122. Further, the detection fiber 126 is coupled to the photosensitive diode 158 so that light energy coupled into the detection fiber 126 is conducted to the photosensitive diode 158.

The monitoring device 110 is operated by coupling the disposable unit 114 and the non-disposable unit 118 such that the source 122 and detection 126 fibers are, respectively, coupled to the light source 154 and the photosensitive diode 158. The binder attached to the outer surface on the source 122 and detection 126 fibers is selected for a desired analyte that is to be monitored. The chemical enhancer in the reservoir 130 is also selectable. The monitoring device 110 is then placed on the skin 166 of the individual or animal to be monitored with the reservoir 130 contacting the skin 166. The transducer 146 is activated to produce ultrasound, preferably in the frequency range of 0.1 to 100 MHz, more preferably 3–30 MHz, and most preferably 5–25 MHz. Optionally, frequency sweeping on other modulations from high to low frequencies can be employed to help drive the enhancers rapidly into the stratum corneum. The average intensity of the ultrasound is preferably in the range of 0.01–5 $W/cm^2$, more preferably 0.05–3 $W/cm^2$. However, higher instantaneous intensities can be employed if the average energy is kept low enough or cooling is applied to prevent damage to the transducer 146 and/or the skin 166. The ultrasound is applied for a time sufficient to drive chemical enhancer from the reservoir 130 into the stratum corneum of the skin 166. Five to twenty minutes or less is ordinarily sufficient to accomplish this. Once the enhancer has permeated the stratum corneum, an optional frequency modulation with the form of the frequency modulation designed to draw analytes from the body into the monitoring device 110 may be applied. Analytes traverse the stratum corneum and are moved toward the transducer 146. As the analytes pass through the disposable unit 114 they come into close proximity to the source 122 and detection 126 fibers. Analytes of the specific type recognized by the binder are then bound on the surface of the fibers. At selected times, the integrated circuit 162 transmits a signal to the light source 154 to transmit light energy. This light energy is conducted through the source fiber 122 and as it does so, evanescent wave energy passes through the wall of the source fiber 122. A portion of this evanescent wave energy is coupled into the detection fiber; however the amount of cross coupling between the source and detection fibers is modulated by the presence of the specific analyte bound to the binder on the surface of both source 122 and detection 126 fibers. The evanescent wave energy captured by the detection fiber 126 is then conducted to the photosensitive diode 158. The photosensitive diode 158 measures the intensity of the captured evanescent wave energy and transmits the intensity measurement to the integrate circuit 162, where the information is stored. Once two or more intensity measurements made at distinct intervals are stored by the integrated circuit 162, the integrated circuit 162 determines the parameters describing the equilibrium curve and calculates the concentration of the specific analyte within the body of the individual. This calculated concentration is then transmitted by a signal to the output device 142 which may comprise one or more of numerous embodiments. For example, the output device can be an LCD, LED, analog panel meter or an audio voice simulation to convey the data to the user. Other examples include an electronic data port, which may provide the output data in a format compatible with other electronic devices utilizing conducting cables to carry this information, a wireless radio frequency transmission, or a modulated light source, where the concentration is displayed or transmitted or otherwise made known thereon.

EXAMPLE 9

An alternate method for detection of an analyte, such as glucose, following the non-invasive sample collection described above, can be achieved through the use of enzymatic means. Several enzymatic methods exist for the measurement of glucose in a biological sample. One method involves oxidizing glucose in the sample with glucose oxidase to generate gluconolactone and hydrogen peroxide. In the presence of a colorless chromogen, the hydrogen peroxide is then converted by peroxidase to water and a colored product.

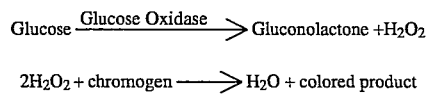

$$2H_2O_2 + \text{chromogen} \longrightarrow H_2O + \text{colored product}$$

The intensity of the colored product will be proportional to the amount of glucose in the fluid. This color can be determined through the use of conventional absorbance or reflectance methods. By calibration with known concentrations of glucose, the amount of color can be used to determine the concentration of glucose in the collected analyte. By testing to determine the relationship, one can calculate the concentration of glucose in the blood of the subject. This information can then be used in the same way that the information obtained from a blood glucose test from a finger puncture is used. Results can be available within five to ten minutes.

EXAMPLE 10

Figure 6A:
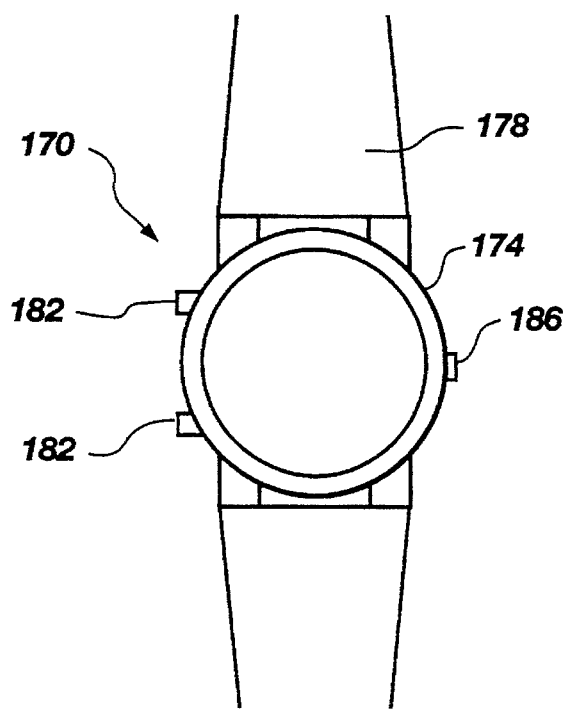
FIG. 6A shows an example of a portable device for enhancing the transdermal flux rate of the skin and collecting an analyte from the body of an individual onto a removable, assayable collection pad.
Figure 6B:
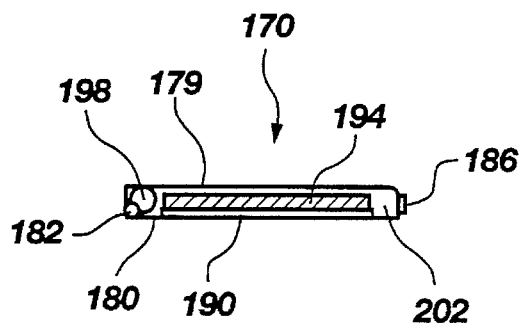
FIG. 6B shows a sectional view of the device of FIG. 6A.

FIGS. 6A and 6B show an illustrative embodiment of a portable device 170 for using this method for collection of the analyte with the aid of ultrasound and chemical enhancer. The device 170 may be embodied in a form having the general appearance and size of a man's wrist watch. Accordingly, the device 170 consists of a case 174 attached to one or two wrist straps 178. The case 174 consists of upper 179 and lower 180 sections which are connected by at least one hinge 182. The upper 179 and lower 180 sections are ordinarily held together by a latch 186. Inside the case 174 are a collecting pad 190, an ultrasonic transducer 194, a battery 198, and assorted electronic components to drive the transducer, control the measurement cycles, process this data, and drive a display 202. The lower section 180 of the case 174 includes an opening over which the collecting pad 190 is positioned. Thus, when the device 170 is strapped to a person's wrist, the collecting pad 190 is in contact with the person's skin. The collecting pad 190 collects the analyte that is drawn from the person's body and also may contain one or more enhancers for enhancing permeability of the skin. Alternatively, enhancers may be stored in a separate reservoir. The transducer 194 is positioned within the case 174 to be directly over the collecting pad 190 so that when the device 170 is strapped to a person's wrist, the collecting pad 190 is between the wrist and the transducer 194. A battery 198 and electronic components 202 are located within the case 174 to provide, respectively, a power source and controls for operating the transducer 194.

This device 170 shown in FIGS. 6A and 6B is designed to be tightly strapped around the wrist so that the device 170 is in intimate contact with the skin (or clamped to a fold of skin on the underside of the forearm). The collecting pad 190 serves as a reservoir for collection of the analyte. In the embodiment illustrated in FIGS. 6A and 6B, the collecting pad 190 also contains a chemical enhancer, one being selected that will not interfere with the subsequent analysis of the analyte of interest. The collecting pad 190, which may be an absorbent pad such as a filter paper, is inserted into the device after the hinged upper 179 and lower 180 sections are opened. Closing the upper 179 and lower 180 sections positions the piezo transducer 194 for producing an ultrasound signal next to the collecting pad 190. In one embodiment, closing the upper 179 and lower 180 sections activates the device 170 and starts a timer. After sufficient time has elapsed, the device 170 shuts itself off and signals the user that the analyte has been collected. The collecting pad 190 could then be removed for immediate or later analysis.

EXAMPLE 11

Figure 7A:
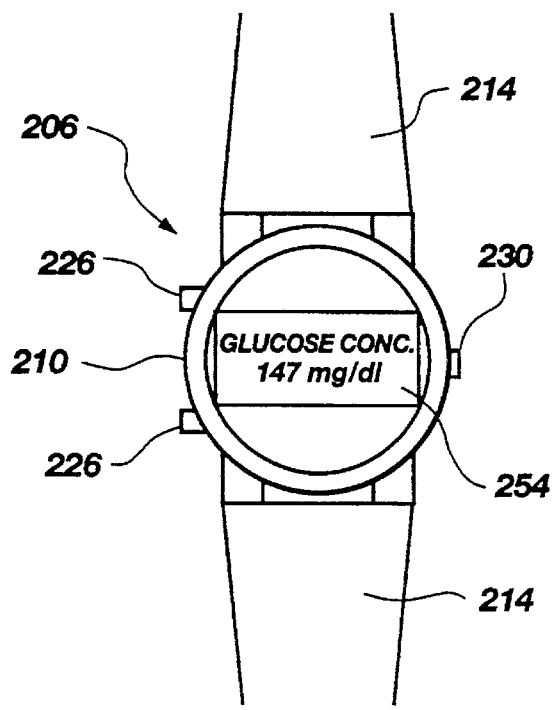
FIG. 7A shows an example of a portable device for enhancing the transdermal flux rate of the skin, collecting an analyte from the body of an individual on a pad containing appropriate chemistry to react with the analyte producing an optically measurable product, and appropriate optics and electronics for quantitating and displaying the concentration of the analyte as a function of the product of the chemical reaction.
Figure 7B:
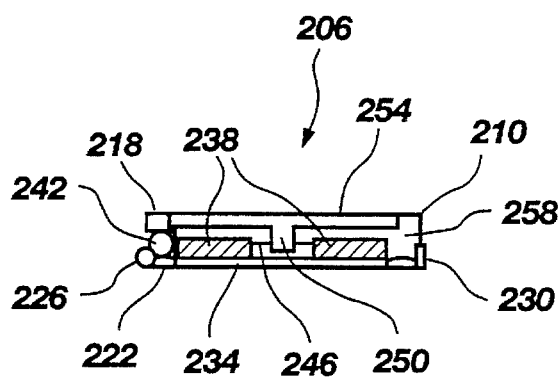
FIG. 7B shows a sectional view of the device of FIG. 7A.

FIGS. 7A and 7B illustrate a similar device 206 with the added feature that the analysis is performed at the time of collection of the analyte. In this illustrative embodiment, glucose is the analyte to be collected and assayed by the glucose oxidase reaction described previously. A color reaction develops as the analyte is collected. The device 206 includes a case 210 attached to one or two straps 214 so that the device can be worn on the wrist. Alternatively, the device 206 may be attached by other conventional means to another part of the body. The case is composed of upper 218 and lower 222 sections connected by at least one hinge 226. The sections 218 and 222 can pivot with respect to each other at the hinge 226 and can be held together by a latch 230. The lower section 222 contains an opening through which glucose may pass from the skin to the interior of the device 206, and enhancers and ultrasound energy may pass to the body. A collection/reaction pad 234 on the interior of the device 206 is positioned with respect to the opening in the lower section 222 so that glucose entering the device 206 from the skin is collected by the pad 234. The pad 234 also contains one or more enhancers, for increasing the permeability of the skin, and the reagents for performing the glucose oxidase assay of glucose concentration. One or more ultrasonic transducers 238 are positioned above the collection/reaction pad 234. Ultrasound produced by the transducers 238 helps the enhancer or enhancers to enter the skin and also helps draw glucose out of the skin toward the collection/reaction pad 234. A battery 242 is contained within the case 210 as a power source for the transducers 238. The case 210 also contains a detector 246 for detecting the results of the glucose oxidase assay, an LED 250 for illuminating a liquid crystal display 254, and electronic components 258 for controlling the transducers 238 and display of the results of the assay on the liquid crystal display 254.

The detector 246 for the glucose oxidase reaction is an optical device for reflectance reading. The electronic components 258 are used to control the piezo transducer 238 and calculate the results from the signal of the detector 246. The transducer 238 can be controlled to provide constant frequency and constant intensity, or can provide swept frequency, swept intensity, or both. The results of the glucose oxidase assay are displayed on a display 254 such as an LCD display on the surface of the device 206, the upper section 218 of the case 210 having an opening through which the display 254 can be seen.

EXAMPLE 12

A visual display or readout of glucose concentration as described in Example 11 will indicate to the wearer or a diagnostician the need for administration of insulin or other appropriate medication. In critical care or other situations where constant monitoring is desired and corrective action needs to be taken almost concurrently, the display may be connected with appropriate signal means which triggers the administration of insulin or other medication in an appropriate manner. For example, there are insulin pumps which are implanted into the peritoneum or other body cavity which can be activated in response to external or internal stimuli. In this manner a complete biomedical control system can be available which not only monitors and/or diagnoses a medical need but simultaneously provides corrective action.

Biomedical control systems of a similar nature could be provided in other situations such as maintaining correct electrolyte balances or administering analgesics in response to a measured analyte parameter such as prostaglandins.

EXAMPLE 13

Similar to audible sound, ultrasound waves can undergo reflection, refraction, and absorption when they encounter another medium with dissimilar properties [D. Bommannan et al., 9 *Pharm. Res.* 559 (1992)]. Reflectors or lenses may be used to focus or otherwise control the distribution of ultrasound energy in a tissue of interest. For many locations on the human body, a fold of flesh can be found to support this system. For example, an earlobe is a convenient location which would allow use of a reflector or lens to assist in exerting directional control (e.g., "pushing" of analytes through the stratum corneum) similar to what is realized by changing ultrasound frequency and intensity.

EXAMPLE 14

Multiple ultrasound transducers may be used to selectively direct the direction of transdermal flux either into the body or from the body. Similar to the system described in Example 11, a fold of skin such as an earlobe allow transducers to be located on either side of the fold. The transducers may be energized selectively or in a phased fashion to enhance transdermal flux in the desired direction. An array of transducers or an acoustic circuit may be constructed to use phased array concepts, similar to those developed for radar and microwave communications systems, to direct and focus the ultrasonic energy into the area of interest.

Therefore, the above examples and illustrated embodiments are but representative of systems which may be employed in the utilization of ultrasound or ultrasound and chemical enhancers in the collection and quantification of analytes for diagnostic purposes. The invention is directed to the discovery that the proper use of ultrasound, particularly when accompanied with the use of chemical enhancers, enables the noninvasive transdermal or transmucosal determination of analytes. However, the invention is not limited only to the specific illustrations. There are numerous enhancer systems some of which may function better than another for detection and withdrawn of certain analytes. However, within the guidelines presented herein, a certain amount of experimentation to obtain optimal enhancers, or optimal time, intensity and frequency of applied ultrasound, as well as modulation of frequency, amplitude and phase of applied ultrasound can be readily carried out by those skilled in the art. Therefore, the invention is limited in scope only by the following claims and functional equivalents thereof.

We claim:

1. A method for non-invasively monitoring the concentration of an analyte in an individual's body comprising the steps of:

(a) enhancing the permeability of a selected area of the individual's body surface to the analyte by means of applying ultrasound to said selected area for a time and at an intensity and a frequency effective to draw the analyte out of the body, wherein said ultrasound is modulated by means of a member selected from the group consisting of frequency modulation, amplitude modulation, phase modulation and combinations thereof;

(b) collecting the analyte; and (c) quantitating the analyte collected.

2. The method of claim 1 wherein step (a) comprises modulating said ultrasound by means of a member selected from the group consisting of frequency modulation and a combination of frequency and amplitude modulation.

3. The method of claim 2 wherein step (a) comprises modulating said ultrasound by frequency modulation.

4. The method of claim 2 wherein step (a) comprises applying said ultrasound at a frequency in the range of about 0.1 to 100 MHz.

5. The method of claim 4 wherein step (a) comprises applying said ultrasound at a frequency in the range of about 3 to 30 MHz.

6. The method of claim 2 wherein step (a) comprises applying said frequency in a sweeping modulation from a lower frequency to a higher frequency for a time sufficient to withdraw analyte from the body.

7. The method of claim 1 wherein step (a) comprises modulating said ultrasound by amplitude modulation.

8. The method of claim 1 wherein step (a) comprises applying said ultrasound at a frequency in the range of about 0.1 to 100 MHz.

9. The method of claim 1 wherein step (a) further comprises using a plurality of transducers for applying ultrasound.

10. The method of claim 1 wherein step (a) comprises applying said ultrasound for a time in the range of about 1 to 30 minutes.

11. The method of claim 1 additionally comprising measuring the amount of analyte collected over intervals of time and from that measurement determining the concentration of analyte in the body.

12. The method of claim 1 further comprising contacting the selected area of the individual's body with a chemical enhancer with the application of the ultrasound to further enhance analyte withdrawal.

13. The method of claim 12 wherein step (a) comprises modulating said ultrasound by means of a member selected from the group consisting of frequency modulation and a combination of frequency and amplitude modulation.

14. The method of claim 13 wherein step (a) comprises modulating said ultrasound by frequency modulation.

15. The method of claim 13 wherein step (a) comprises applying said ultrasound at a frequency in the range of about 0.1 to 100 MHz.

16. The method of claim 15 wherein step (a) comprises applying said ultrasound at a frequency in the range of about 3 to 30 MHz.

17. The method of claim 13 wherein step (a) comprises applying said frequency in a sweeping modulation.

18. The method of claim 13 wherein step (a) comprises modulating said ultrasound by frequency modulation, wherein the frequency is first modulated from a higher to a lower frequency for a time sufficient to enable the chemical enhancer to penetrate the body surface followed by modulating the frequency from a lower to a higher frequency for a time sufficient to withdraw analyte from within the body surface.

19. The method of claim 18 additionally comprising measuring the amount of analyte collected over intervals of time and from that measurement determining the concentration of analyte in the body.

20. The method of claim 19 further comprising collecting the analyte through binding of the analyte to a binder.

21. The method of claim 20 wherein step (c) comprises binding the analyte to said binder, wherein the binder is disposed on source and detection optical fibers and bound analyte attenuates an amount of light energy captured by the detection fiber, wherein quantity of attenuation is a measurement of analyte collected.

22. The method of claim 12 wherein step (a) comprises modulating said ultrasound by amplitude modulation.

23. The method of claim 12 wherein step (a) comprises applying said ultrasound at a frequency in the range of about 0.1 to 100 MHz.

24. The method of claim 12 wherein step (a) further comprises using a plurality of transducers for applying ultrasound.

25. The method of claim 12 wherein step (a) comprises applying said ultrasound for a time in the range of about 1 to 30 minutes.

26. The method of claim 12 wherein step (c) comprises binding the analyte to said binder, wherein the analyte is glucose.

27. The method of claim 26 wherein step (c) comprises quantitating the analyte collected by a colorimetric assay with glucose oxidase.

* * * * *